United States Patent
Dennerlein et al.

(10) Patent No.: US 9,131,910 B2
(45) Date of Patent: Sep. 15, 2015

(54) METHOD FOR OBTAINING A 3D RECONSTRUCTION OF AN OBJECT, AND X-RAY DEVICE

(75) Inventors: Frank Dennerlein, Forchheim (DE); Ernst-Peter Rührnschopf, Erlangen (DE)

(73) Assignee: SIEMENS AKTIENGESELLSCHAFT, München (DE)

( * ) Notice: Subject to any disclaimer, the term of this patent is extended or adjusted under 35 U.S.C. 154(b) by 861 days.

(21) Appl. No.: 13/308,747

(22) Filed: Dec. 1, 2011

(65) Prior Publication Data

US 2012/0140875 A1 Jun. 7, 2012

(30) Foreign Application Priority Data

Dec. 3, 2010 (DE) .......................... 10 2010 062 402

(51) Int. Cl.
*A61B 6/03* (2006.01)
*A61B 6/00* (2006.01)
*G06T 11/00* (2006.01)

(52) U.S. Cl.
CPC ............... *A61B 6/4007* (2013.01); *A61B 6/032* (2013.01); *A61B 6/4035* (2013.01);
(Continued)

(58) Field of Classification Search
CPC .... A61B 6/4007; A61B 6/4035; A61B 6/482; A61B 6/032; A61B 6/4021; A61B 6/03; A61B 6/4078; G06T 2211/408; G21K 1/043; G01N 23/046; G01N 2223/419; G01T 1/2985; G01T 1/1611; G01T 1/1644; G01T 1/1648; G01T 1/1618; G01T 1/169; G01T 1/20; G01T 1/295; G01T 7/005; G01T 1/1603; G01T 1/1641; G01T 1/1642; G01T 1/1647; G01T 1/2018; G01T 1/362
USPC ............. 378/9, 16, 5, 15, 98.9, 137, 156, 159
See application file for complete search history.

(56) References Cited

U.S. PATENT DOCUMENTS 4,255,664 A * 3/1981 Rutt et al. .......................... 378/5
7,476,023 B1 * 1/2009 Canfield et al. ............... 378/203
(Continued)

FOREIGN PATENT DOCUMENTS

| DE | 102008051157 A1 | 11/2009 |
| DE | 102008056891 A1 | 5/2010 |
| JP | 2007268241 A * | 10/2007 |

OTHER PUBLICATIONS

Granton et al., Implementation of dual- and triple-energy cone-beam micro-CT for postreconstruction material decomposition, 2008, Medical Physics, vol. 35, No. 11, p. 5030-5042.*
(Continued)

*Primary Examiner* — David J Makiya
*Assistant Examiner* — John Corbett

(57) ABSTRACT

3D reconstructions can be calculated from grayscale X-ray images taken at different angular positions of an X-ray source and detector rotatable about a common axis. In the present case, X-ray radiation is applied to the object to be imaged such that one half of the X-ray detector receives radiation which differs in one characteristic from the radiation received by the second half of the detector via the object. A kind of dual-energy imaging can then be carried out in a single pass through the angular positions, enabling two 3D reconstructions to be generated simultaneously and then merged.

6 Claims, 3 Drawing Sheets

(52) U.S. Cl.
CPC .............. *A61B 6/4233* (2013.01); *A61B 6/482* (2013.01); *G06T 11/005* (2013.01); *A61B 6/03* (2013.01); *A61B 6/4028* (2013.01); *A61B 6/4441* (2013.01); *G06T 2211/408* (2013.01)

(56) References Cited

U.S. PATENT DOCUMENTS

| | | | |
|---|---|---|---|
| 7,620,141 | B2 | 11/2009 | Gotoh |
| 2003/0048868 | A1* | 3/2003 | Bailey et al. ................. 378/65 |
| 2003/0147502 | A1* | 8/2003 | Heismann et al. ........... 378/156 |
| 2005/0084073 | A1* | 4/2005 | Seppi et al. .................. 378/156 |
| 2005/0094769 | A1* | 5/2005 | Heismann et al. ........... 378/158 |
| 2006/0008047 | A1* | 1/2006 | Zhou et al. .................... 378/10 |
| 2007/0147581 | A1* | 6/2007 | Ellenbogen et al. ........... 378/19 |
| 2009/0135994 | A1* | 5/2009 | Yu et al. .......................... 378/5 |
| 2010/0119035 | A1* | 5/2010 | Karch ............................. 378/19 |

OTHER PUBLICATIONS

Chen et al., Dual-basis-material decomposition for dual-kVp cone-beam CT breast imaging, 2005, SPIE, vol. 5745, pp. 1322-1333.*

Chen et al., Cone-beam volume CT breast imaging: Feasibility study, 2002, Medical Physics, vol. 29, No. 5, pp. 755-770.*

Ross et al., Design and performance characteristics of a digital flat-panel computed tomography system, 2006, Medical Physics, vol. 33, No. 6, pp. 1888-1901.*

Du et al., A quality assurance phantom for the performance evaluation of volumetric micro-CT systems, 2007, Physics in Medicine and Biology, vol. 52, pp. 7087-7108.*

Feldkamp et al., Practical cone-beam algorithm, 1984, Journal of the Optical Society of America, vol. 1, No. 6, pp. 612-619.*

Cho et al., Cone-Beam CT from Width-Truncated Projections, 1996, Computerized Medical Imaging and Graphics, vol. 20, No. 1, pp. 49-57.*

Machine translation of JP2007-268241A.*

A. C. Kak et al.; "Principles of Computerized Tompgraphic Imaging"; Kapitel 3, Algorithms for Reconstruction with Nondiffracting Sources; IEEE Press, New York, 1988, ISBN 0-87942-198-3, pp. 49-112.

Press et al.; "Numerical Recipes—The Art of Scientific Computing / (FORTRAN Version)"; Chapter 9.6 Newton-Raphson Method for Nonlinear Systems of Equations, pp. 268-273; Cambridge University Press; 052138330-7, 1989.

Frank Dennerlein, Holger Kunze, "Cone beam reconstruction with displaced flat panel detector", Int. Conf. Fully Tree-Dimensional Image Reconstruction in Radiology and Nuclear Medicine, Peking, China, Sep. 2009; p. 138.

Seungryong Cho, Dan Xia, Erik Pearson, Charles A. Pelizzari, and Xiaochuan Pan; "Half-fan-based Region-of-interest Imaging in Circular Cone-beam CT for Radiation Therapy"; Proc. of the Fully 3D, Beijing 2009, pp. 385-388.

* cited by examiner

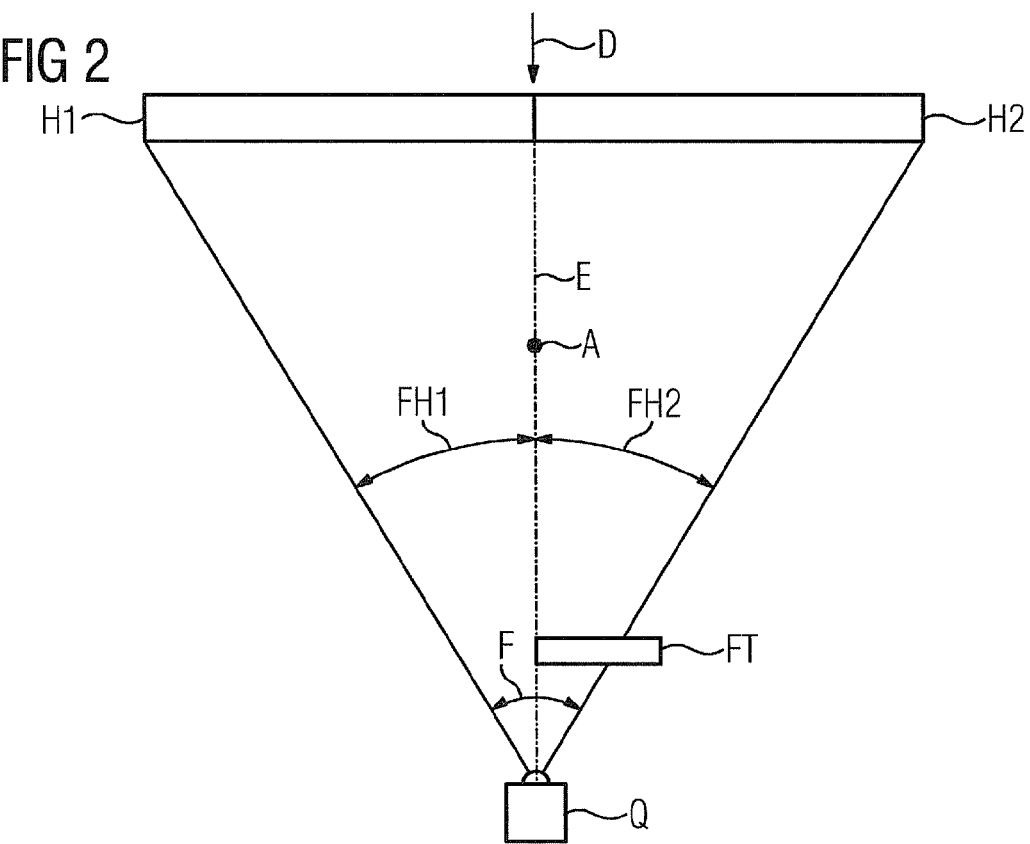
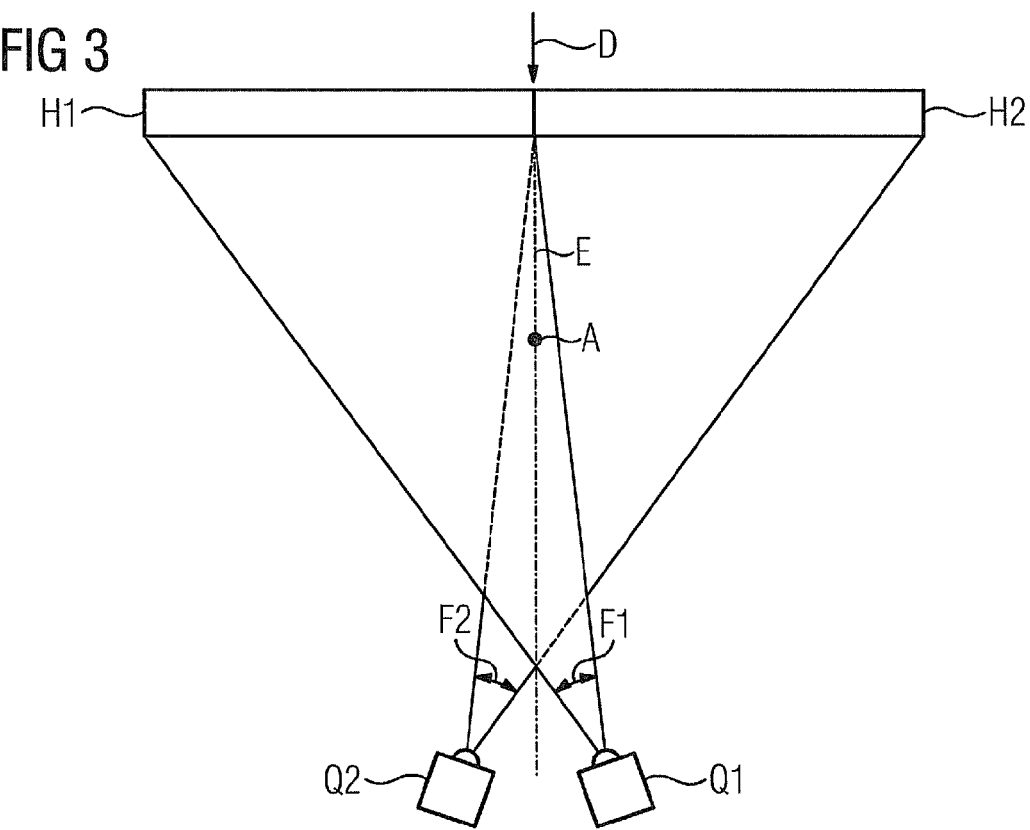

METHOD FOR OBTAINING A 3D RECONSTRUCTION OF AN OBJECT, AND X-RAY DEVICE

CROSS REFERENCE TO RELATED APPLICATIONS

This application claims priority of German application No. 10 2010 062 402.0 filed Dec. 3, 2010, which is incorporated by reference herein in its entirety.

FIELD OF INVENTION

The invention relates to a method for obtaining a 3D reconstruction of an object using an X-ray device.

BACKGROUND OF INVENTION

The 2D grayscale X-ray image data (i.e. the projection data) usually undergoes a filtering step using conventional mathematical signal processing methods. The mathematical filtering is a convolution with a suitable function, said function indicating how different frequencies are to be weighted. Mathematical filtering is followed by actual 3D back projection. The entire process is also known as filtered back projection as described, for example, in the book by A. C. Kak and M. Slaney, "Principles of Computerized Tomographic Imaging", IEEE Press, 1988.

It has now been recognized that, to reconstruct a region of interest of an object, it suffices to map only half of said region of interest in the grayscale X-ray images, provided that 2D grayscale X-ray images are taken at angular positions of X-ray source and flat-panel X-ray detector over a full circle (i.e. through 360°).

This is based on the recognition that each ray which passes from the X-ray source of a particular angular position to a detector element on the flat-panel X-ray detector has a correspondence at another angular position where the radiation passes in the opposite direction, but on the same path.

This fact is utilized e.g. in DE 10 2008 051 157 A1 to virtually enlarge a detector, cf. also the article by Holger Kunze and Frank Dennerlein: "Cone beam reconstruction with displaced flat panel detector." Proc. of the Fully 3D, 2009. In the case of the "differentiated back projection" method as described in Seungryong Cho, Dan Xia, Erika Pearson, Charles A. Pelizzari, and Xiaochuan Pan: "Half-fan-based Region-of-interest Imaging in Circular Cone-beam CT for Radiation Therapy", Proc. of the Fully 3D, 2009, there does not even have to be an overlapping region, for example.

It is now known that a 3D reconstruction does not necessarily provide all the information necessary for an assessment. This problem is frequently overcome by obtaining a second 3D reconstruction. For example, a first 3D image dataset is acquired using X-rays of a particular frequency or energy, and a second X-ray image dataset is obtained using X-rays of a different frequency or energy. With this so-called dual-energy imaging, different materials can then be separated, as one material attenuates the X-ray radiation of one frequency slightly more than that of another frequency, and in the case of another material precisely the opposite may apply. Using suitable image fusion methods, this enables in particular different materials to be separated and image quality improvements to be achieved.

DE 10 2008 056 891 A1 describes a computed tomography (CT) scanner in which an X-ray filter is used to produce an unfiltered and a filtered radiation component of a fan beam, said radiation components having different X-ray spectra. In order to operate the scanner in a dual-energy mode, the processing unit analyzes a measurement signal of the unfiltered radiation component separately from a measurement signal of the filtered radiation component. An X-ray detector is of curved design to detect the entire radiation.

U.S. Pat. No. 7,620,141 B2 discloses a computer tomograph in which a flat-panel X-ray detector is used and the tomograph's X-ray source is operated at different voltages to generate two different kinds of X-ray fan beams alternately one after the other.

U.S. Pat. No. 7,476,023 B1 discloses an X-ray emitter for an X-ray apparatus, comprising two X-ray sources. The X-ray sources are interconnected such that their beams always have the same focal spot. In conjunction with a dual-energy mode, it is proposed, because of the common focus, to generate beams with different energy levels consecutively.

However, acquiring a plurality of 3D image datasets is very time-consuming.

SUMMARY OF INVENTION

The object of the invention is to demonstrate a way of acquiring necessary image information in a shorter time.

This object is achieved in one aspect by a method and in another aspect by the X-ray imaging devices as claimed in the claims.

For obtaining a 3D reconstruction of an object, an X-ray source or a flat-panel X-ray detector are rotatable about a common axis. 3D reconstructions are basically datasets in which grayscale values are assigned to individual volume elements in space. Said grayscale values are indicative of the local tissue density of a patient or the local material density of an inanimate object. Generating 3D reconstructions requires capturing a sequence of individual (grayscale) X-ray images from different angles. These individual two-dimensional grayscale X-ray images are also termed projections, because the three-dimensional space has been mapped onto a two-dimensional flat-panel X-ray detector. The projections are usually obtained in a defined manner at predetermined angles with respect to a spatial axis, wherein at least 180° and often even 360° are traversed. Although the X-ray device is typically implemented as a computed tomography (CT) system, the present invention is equally applicable to an X-ray imaging system in the form of an X-ray angiography system, the X-ray source and the flat-panel X-ray detector being disposed, for example, on an X-ray C-arm.

The method according to the invention is characterized in that
  the X-ray detector is a flat-panel X-ray detector,
  at least two of the plurality of angular positions are spaced 160° and 200° apart,
  the data for a second 3D reconstruction is generated using image data obtained by the second part of the flat-panel X-ray detector, and
  data of the two 3D reconstructions is used to obtain a (namely the wanted) 3D reconstruction of the object (which is therefore a merged, i.e. fused, 3D reconstruction).

The invention is based on the known insight that it suffices for a 3D reconstruction if only part of an object is mapped in order to map different parts of the same object differently, namely onto one and the same 2D grayscale X-ray images which are the result of executing imaging steps. It is then unnecessary to carry out a pass of obtaining grayscale X-ray images for one 3D reconstruction and then carry out a second pass under changed conditions for the second 3D reconstruction. Instead, all this takes place in a single pass. It is not even necessary here for the first 3D reconstruction to be calculated first and then the second 3D reconstruction to be calculated completely before the merged 3D reconstruction is calculated. Rather, the data from the two 3D reconstructions can be merged voxel-wise (referred to the volume elements according to which the 3D reconstruction is defined) even during ongoing operation.

As mentioned in the introduction, a complete pass must be executed, e.g. a pass through the angular positions from 0° to (almost) 360°, namely in uniform increments of 0.5° to 2°. It can be specified as a minimum requirement that at least two of the plurality of angular positions are spaced 160° and 200° apart.

For obtaining the 3D reconstructions it is advantageous if the axis of rotation runs through a plane perpendicular to the flat-panel X-ray detector and this plane subdivides the flat-panel X-ray detector into the two parts mentioned above.

The characteristic by which the X-ray radiation applied to one part of the object differs from the X-radiation applied to another part of the object may relate to the spectral composition, i.e. to the ratio of the intensities at individual frequencies. It may also equally relate to the intensity at a predetermined wavelength or frequency, or even to the total intensity, and lastly also to the radiation time (emission from the X-ray source and irradiation of the object).

In a first embodiment, a filter can be used as a means of effecting this differential application of the radiation. A filter is particularly easy to mount in a beam path. Thus it is preferably provided that the flat-panel X-ray detector receives an X-ray fan beam from an X-ray source, a sub-beam of which undergoes filtering and the rest does not, or a sub-beam of which undergoes filtering different from that of the rest of the X-ray fan beam. In particular, a shaping filter can also be used. A shaping filter is a filter which filters beam emanating from an X-ray source differently depending on the direction in which they are emitted. This compensates for the differential attenuation of the X-rays which is caused by rays emitted in different directions passing through the object over a different length. The shaping filter usually has an non-homogeneous thickness even if it consists of a homogeneous material. If a sub-beam is to undergo filtering different from the rest of the X-ray fan beam, in particular an asymmetrical shaping filter can be used in the invention. Said filter therefore usually has a non-homogeneous thickness, and this not even symmetrical to the central axis or plane which is defined by an X-ray beam perpendicularly incident on the X-ray detector. In an additional aspect of the invention, an asymmetrical shaping filter of this kind is provided for the first time, either per se, or placed in an X-ray device where a required position must be defined with respect to a shaping filter.

Alternatively to the first embodiment of the invention, it can be provided according to a second embodiment of the invention that the X-ray device has two X-ray sources, one part of the flat-panel X-ray detector receiving an X-ray fan beam from one X-ray source and the other part of the flat-panel X-ray detector receiving an X-ray fan beam from the other X-ray source.

For the invention, the 3D reconstruction is preferably produced in per se known manner by means of filtered back projection.

The X-ray device comprises an X-ray source and a flat-panel X-ray detector which are rotatable about a common axis, and a filter which can be positioned such that X-radiation filtered by said filter is incident on a first part of the flat-panel X-ray detector but not on a second part of the flat-panel X-ray detector. By contrast, the X-ray device has two X-ray sources and a flat-panel X-ray detector which are rotatable about a common axis, X-ray beams emitted by the first X-ray source being received (in particular only) by a first part of the flat-panel X-ray detector and X-ray beams emitted by the second X-ray source being received (in particular only) by a second part of the flat-panel X-ray detector. In the case of both the X-ray device, a processing unit is provided which is designed to generate data for two 3D reconstructions on the basis of a plurality of grayscale images of an object that are obtained by the flat-panel X-ray detector, wherein, for the data of one 3D reconstruction, grayscale values of the grayscale images which were obtained using the first part of the flat-panel X-ray detector are used and, for the data of the second 3D reconstruction, grayscale values of the grayscale images obtained using the second part of the flat-panel X-ray detector are used. The advantages mentioned in respect of the method according to the invention are equally applicable to both X-ray devices. Here it suffices for two 3D reconstructions to be available, it being preferably provided that the processing unit combines, i.e. merges, the two 3D reconstructions into one 3D reconstruction.

BRIEF DESCRIPTION OF THE DRAWINGS

Preferred embodiments will now be described in greater detail with reference to the accompanying drawings in which:

FIG. 2 is a schematic diagram for explaining a first embodiment of the method according to the invention, FIG. 3 is a schematic diagram for explaining a second embodiment of the method according to the invention.

DETAILED DESCRIPTION OF INVENTION

Figure 1:
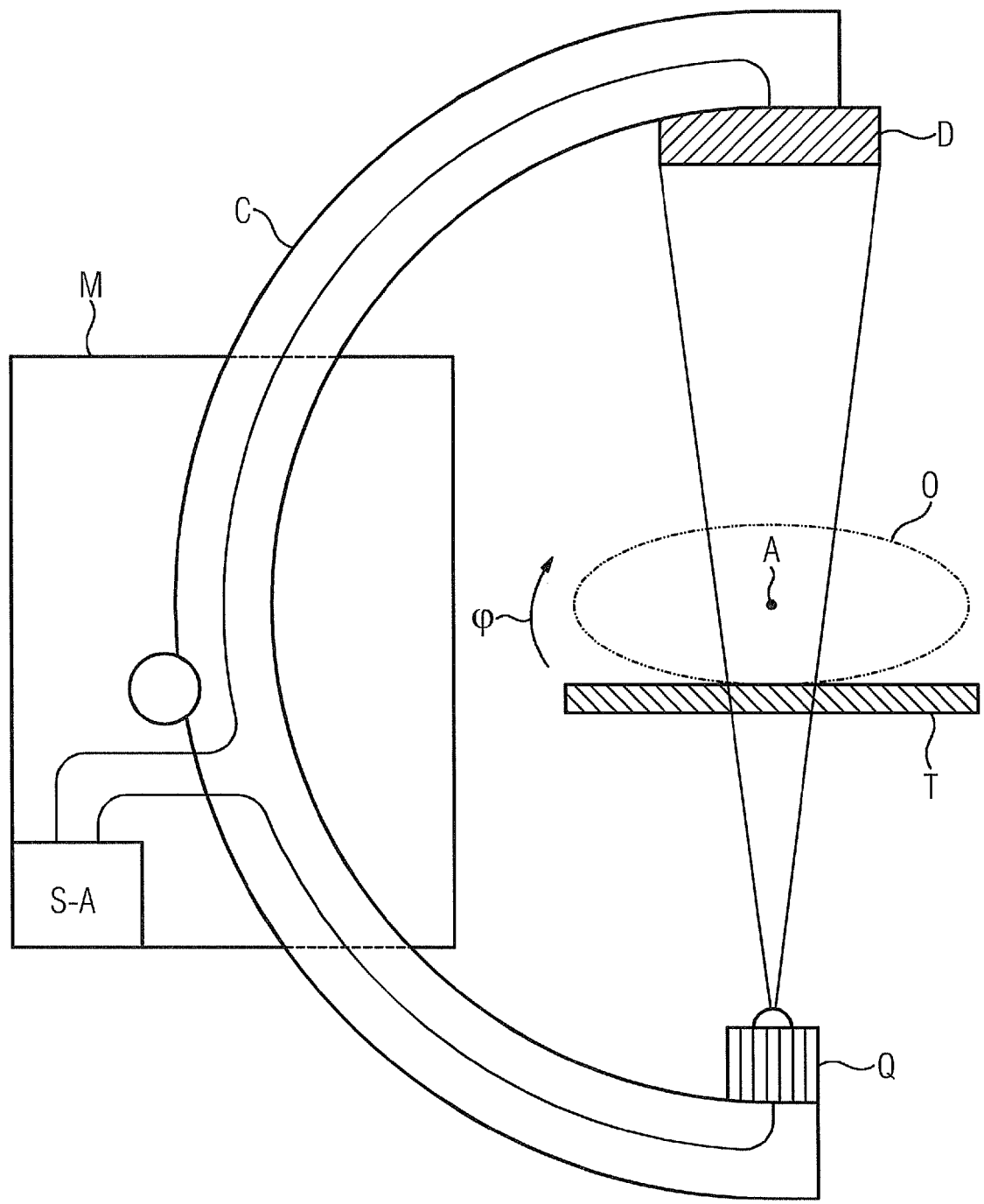
FIG. 1 shows an X-ray device which can be implemented according the invention.

An X-ray device shown in FIG. 1 is used for imaging an object O lying on a table T. This can be a patient but can also be an inanimate object. The device comprises an X-ray (radiation) source Q and an X-ray detector D which are interconnected, in this case via a C-arm C which can be moved by a mechanical device M (not shown) such that it can assume angular positions φ about an axis of rotation A, in this case any angular positions. The X-ray source Q is controlled by a control and processing device S-A, and the detector which in this case is to be implemented as a flat-panel X-ray detector transmits measurement data to the control and processing device S-A. The latter is designed to effect execution of the method according to the invention.

If the C-arm is successively rotated in increments of 0.5° about the axis of rotation A and takes an X-ray (grayscale) image in each case, a 3D reconstruction can then be obtained. However, there is data redundancy. For a full-circle rotation, it suffices if the data of one detector half H1, H2 is used.

In the present example, this can be used to obtain data of different kinds by means of the detector halves H1 and H2: it is ensured that different kinds of X-ray radiation are applied to the object O depending on whether the rays subsequently reach the detector half H1 or the detector half H2.

In a first embodiment of the invention, one half FH1 of an X-ray fan beam designated F as a whole is transmitted to the detector half H1 (the object O not being shown in FIG. 2 for reasons of illustration simplicity). The second half FH2, on the other hand, is filtered by a filter FT so that particular frequencies are attenuated. The second half of the X-ray fan beam F, FH2 is transmitted to the second half H2 of the X-ray detector D. In this case the plane E which divides the detector D into the two halves H1, H2 shall contain the axis of rotation A. A particularly good reconstruction is then possible: the control and processing device S-A initiates the taking of X-ray images through 360° in 0.5° increments. All the data acquired by the half H1 of the detector D is now used to obtain a 3D reconstruction. This is straightforwardly possible— compare, for example, the methods quoted in the above mentioned articles by Kunze and Dennerlein on the one hand and Cho et al. on the other. Using the data obtained from the second detector half H2, a second 3D reconstruction of the object O is obtained. This differs from the first 3D reconstruction because, for example, regions which attenuate X-rays of a frequency filtered out by the filter FT are more clearly visible in one reconstruction H1 than in the other reconstruction H2. An optimum 3D reconstruction can therefore be achieved by merging the two 3D reconstructions.

Alternatively, in a second embodiment of the invention as shown in FIG. 3, it is possible to provide two X-ray sources Q1, Q2 which emit two different X-ray fan beams F1 and F2, the first beam F1 being incident on the first half H1 of the detector D and the second fan beam F2 being incident on the second half H2 of the detector D, a slight overlap being acceptable. The two sources Q1 and Q2 are preferably disposed mirror-symmetrically with respect to a plane E in which the axis of rotation A lies in a plane perpendicular to the surface of the detector D.

It is equally possible to use a single X-ray source, but in this case implementing focus deflection in accordance with the flying-spot principle.

Figure 4:
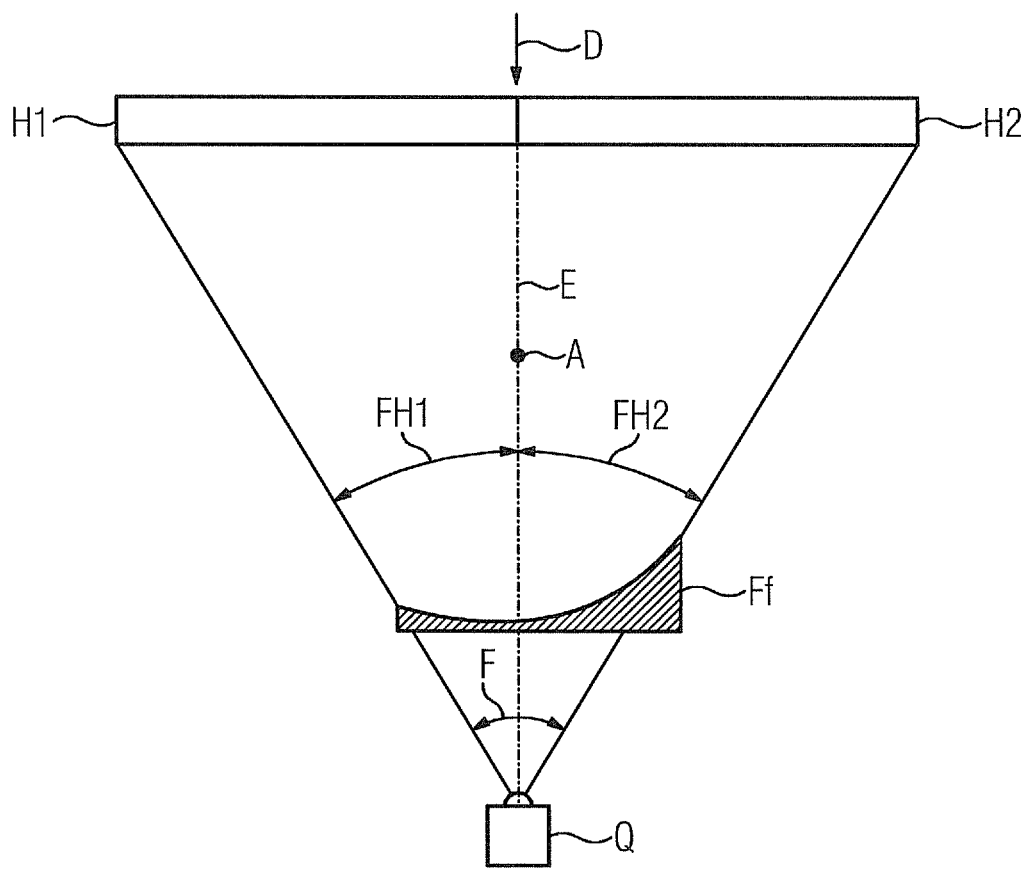
FIG. 4 is a schematic diagram for explaining in particular a variant of the first embodiment of the method according to the invention.

In a variant of the embodiments, in particular of the first, an asymmetrical shaping filter Ff can be provided for two X-ray fan beams such that one X-ray fan beam can be filtered differently from the other by shaping filtering. FIG. 4 shows how the shaping filter Ff, which is asymmetrical with respect to the plane E and consists of homogeneous material, is slightly less thick toward the outside with respect to the first half FH1 of the X-ray fan beam than with respect to the second half FH2. This enables different filtering objectives for the two halves to be achieved. For example, one half of the filter can be used for intensity equalization with respect to a particular object shape, the other for adjustment in the spectral composition of the radiation reaching the detector or adjustment of any kind in respect of another object shape.

The invention makes dual-energy imaging possible without the need for a plurality of passes by the X-ray C-arm.

The invention claimed is:

1. An X-ray device, comprising:
an X-ray source that emits X-ray radiation;
a flat-panel X-ray detector that is rotatable about a common axis of rotation with the X-ray source for acquiring image data of an object, wherein the flat-panel X-ray detector is subdivided into a first part and a second part by a plane that is perpendicular to the flat-panel X-ray detector and has the axis of rotation runs through the plane; and
a processing unit that generates:
   a first 3D image reconstruction using image data acquired by the first part of the flat-panel X-ray detector,
   a second 3D image reconstruction using image data acquired by the second part of the flat-panel X-ray detector,
   a 3D image reconstruction using the first 3D image reconstruction and the second 3D image reconstruction,
wherein the X-ray source comprises a first X-ray source and a second X-ray source, and
wherein the first X-ray source and the second X-ray source are disposed mirror-symmetrically with respect to the plane so that the first part of the flat-panel X-ray detector only receives a first X-ray radiation emitted from the first X-ray source and the second part of the flat-panel X-ray detector only receives a second X-ray radiation emitted from the second X-ray source that is different from the first X-ray radiation.

2. The device as claimed in claim 1, wherein the first x-ray source has a characteristic of the X-ray radiation that is different in spectral composition, intensity at a particular wavelength, overall intensity, or duration from that of the second x-ray source.

3. The device as claimed in claim 1, wherein the X-ray radiation from the first X-ray source and the second X-ray source are X-ray fan beams.

4. The device as claimed in claim 1, wherein the first X-ray source and the second X-ray source are contained in a single X-ray source and is implemented in accordance with the flying-spot principle.

5. The X-ray device as claimed in claim 1, wherein the 3D reconstruction is generated by filtered back projection.

6. The X-ray device as claimed in claim 1, wherein the 3D reconstruction is generated by combining the first 3D reconstruction and the second 3D reconstruction.

* * * * *